United States Patent [19]

Dougherty

[11] Patent Number: 5,257,970
[45] Date of Patent: Nov. 2, 1993

[54] IN SITU PHOTODYNAMIC THERAPY

[75] Inventor: Thomas J. Dougherty, Grand Island, N.Y.

[73] Assignee: Health Research, Inc., Buffalo, N.Y.

[21] Appl. No.: 865,918

[22] Filed: Apr. 9, 1992

[51] Int. Cl.$^5$ .............................................. A61N 1/30
[52] U.S. Cl. ..................................... 604/20; 604/49; 424/450; 540/145
[58] Field of Search ........................... 604/20, 21, 49; 128/898; 424/450; 540/145

[56] References Cited

U.S. PATENT DOCUMENTS

| | | | |
|---|---|---|---|
| 4,558,690 | 12/1985 | Joyce | 128/898 |
| 4,649,151 | 3/1987 | Dougherty et al. | 514/410 |
| 4,801,459 | 1/1989 | Liburdy | 424/450 |
| 4,866,168 | 9/1989 | Dougherty et al. | 540/145 |
| 4,889,129 | 12/1989 | Dougherty et al. | 128/664 |
| 4,891,043 | 1/1990 | Zeimer et al. | 604/20 |
| 4,932,934 | 6/1990 | Dougherty et al. | 604/21 |
| 4,935,407 | 6/1990 | Luider et al. | 514/58 |
| 5,004,565 | 4/1991 | Schaap | 252/700 |
| 5,006,473 | 4/1991 | Bouma et al. | 436/516 |
| 5,015,478 | 5/1991 | Jori et al. | 604/49 |
| 5,041,078 | 8/1991 | Matthews et al. | 604/4 |
| 5,145,863 | 9/1992 | Dougherty et al. | 604/49 |

OTHER PUBLICATIONS

Fidler, I. J., "Therapy of Disseminated Melanoma by Liposome-Activated Macrophages", World Journal of Surgery, vol. 16, No. 2 (Mar.-Apr.) pp. 270-276 1992.
Dinney et al., "Immunotherapy of Murine Renal Adenocarcinoma by Systemic Administration of Lipsomes Containing the Synthetic Macrophage Activator CGP-31362 or CGP-19835A In Combination with Interleukin-2 or Gamma-Interferon", Cancer Research, vol. 52, No. 5 pp. 1155-1161, Mar. 1, 1992.
Chemi- and Bioluminescence, edited by John G. Burr, Marcel Dekker Inc., New York, 1985 (copies of the pertinent pages of this book are attached).

*Primary Examiner*—C. Fred Rosenbaum
*Assistant Examiner*—Michael Rafa
*Attorney, Agent, or Firm*—James F. Mudd; Mark G. Bloom; Michael L. Dunn

[57] ABSTRACT

The process of photodynamic therapy (PDT) is conducted by the step of:

1) separately encapsulating at least one activation component for said photodynamic therapy process in a liposome;
2) injecting a photosensitizer into a human or animal host;
3) injecting the liposome encapsulated components systemically into the same human or animal host; and
4) heating the site of the tumor to melt the liposome encapsulated components to permit mixing of the activation components.

The mixing of the activation components can result in:

a) energy transfer to the previously injected photosensitizer;
b) emission of light and absorption of said light by the previously injected photosensitizer; and
c) direct formation of at least one cytotoxic species that functions against the tumor.

The heating of the site of the tumor is accomplished by one of the following methods: laser, ultra sound, radiofrequency or microwave frequency. Photofrin photosensitizer is a preferred photosensitizer.

9 Claims, No Drawings

IN SITU PHOTODYNAMIC THERAPY

BACKGROUND OF THE INVENTION AND PRIOR ART

Photodynamic therapy (PDT) is being used experimentally to treat a wide variety of malignant tumors and certain other diseases, such as psoriasis and papillomatosis. This technology is disclosed in U.S. Pat. Nos. 4,649,151; 4,866,168; 4,889,129 and 4,932,934, the disclosures of which are incorporated herein by reference.

The PDT method utilizes a photosensitizer which accumulates in tumors and can be activated by an appropriate light source, generally a laser. In general, the treatment is limited by the need to deliver light internally, for example, by fiber optics through endoscopes. Further, depth of penetration is limited by the optical properties of the tumor tissue and is generally in the 2–5 mm range. While fiber optics can be inserted directly into tumors to deliver the light to bulky tumors, this is often not possible for technical reasons, such as tumor location and size.

U.S. Pat. No. 4,801,459 describes the release of drugs from liposomes using RF or microwaves to break the liposome. However, this patent says nothing about causing local reaction of two or more components to generate excited states or light to "activate" a material already in the tissue, such as a photosensitizer.

U.S. Pat. No. 4,891,043 requires a laser to "break" a liposome to deliver drugs or dyes to a site.

The following U.S. Pat. Nos. show the encapsulation of selected compounds in liposomes: 4,935,407; 5,004,565 and 5,006,473.

It has been established for many years that certain biological processes generate light, for example, firefly luminescence via reaction of luciferase with luciferin. Also, it is well known that certain chemical reactions generate light via excited intermediate species, for example, thermal decomposition of 1,2-dioxetanes and oxidation of malonic acid. Further, in some cases, the excited states can be trapped, causing excitation of the trapping agent. Complete descriptions of numerous such reactions can be found in Chemi- and Bioluminescence, edited by John G. Burr, Marcel Dekker Inc., New York, 1985, the disclosure of which is incorporated herein by reference. However, these types of reactions cannot be used with all photosensitizers since some photosensitizers accumulate in normal tissues as well as in tumors.

It is a purpose of the invention to allow photodynamic therapy to be carried out without the necessity of using expensive and difficult to maintain laser systems.

It is another purpose of the invention to allow photodynamic therapy to treat distant metastases, that is, tumors in difficult to reach locations or where the exact location of the tumor is unknown.

It is a further purpose of the invention to allow photodynamic therapy to treat larger tumor masses.

SUMMARY OF THE INVENTION

The invention involves photodynamic therapy (PDT) conducted by the process of:

1) separately encapsulating the separate components of an activation system for photodynamic therapy in heat-sensitive liposomes;

2) injecting a photosensitizer into a host to be treated;

3) injecting the liposome encapsulated materials systemically into the same human or animal host; and 4) melting the liposomes selectively at a tumor site within the host using direct heat-producing systems.

When the liposome encapsulated components are co-melted at the tumor site, mixing of the components of the activation system occurs, thereby causing:

a) light emission and absorption by the previously injected photosensitizer;

b) energy transfer to the previously injected photosensitizer; or c) direct formation of a cytotoxic species which can interact with a tumor.

DETAILED DISCLOSURE OF THE INVENTION

It is the process of this invention, to 1) encapsulate the components of the activating systems for photodynamic therapy separately in heat-sensitive liposomes (see e.g., Radiation Research 122: 161, 1990); 2) inject the liposome encapsulated materials systemically, and 3) 'melt' the liposomes (41°–45° C.) selectively at the tumor site using direct heat-producing systems. When the liposomes are co-melted at the tumor site, mixing of the 'activator system' (generally two or three or more component systems) occurs causing a) light emission and absorption by the previously injected photosensitizer; b) energy transfer to the previously injected photosensitizer; or c) direct formation of a cytotoxic species.

While two or three or more activator components are mentioned above, it is possible that only one activator component be introduced to the host via the liposome encapsulation method, because another activator component, such as macrophages, may already be present in the tumor or associated tissue. In the later case, only one activator need be encapsulated. This encapsulated component would react with the other activator component or components already present in the tissue.

Requirements for such activator systems are as follows. 1) The light emitted by the activating system should be in the range absorbed by the photosensitizer (the emission spectrum and intensity of the light emitted by the activator system can be adjusted with a third component). 2) For energy transfer, the energy of the intermediate excited species produced by the activator system must be near or greater than the energy of either the singlet or triplet state of the photosensitizer. 3) Alternatively, the activator must be capable of undergoing a reaction which directly produces the cytotoxic species either with or without added photosensitizer.

Following are components suitable for use in the practice of the invention.

Photosensitizers

The preferred photosensitizer useful in the invention is Photofrin®, the tradename for an oligomeric mixture of porphyrins.

Also useful are crude mixtures of porphyrins, also known as hematoporphyrin derivative (Hpd). These compounds, when injected into experimental animals with transplanted tumors or into humans with cancerous tumors tend to accumulate selectively in a wide variety of such malignant solid tumors.

The following properties of photosensitizers are important for use in humans:

1. low toxicity;
2. photophysically efficient, that is, high yield of singlet oxygen or other reactive species;

3. activatable by tissue-penetrating light (>600 nm); and 4. proper pharmacokinetics; that is, relatively selective for tumors and not cleared too rapidly.

The following properties, while not essential, are highly desirable:

1. easily formulated for systemic use;
2. low cost;
3. high extinction coefficient in the red or near infrared; and
4. availability of easy to use light sources for activation.

Additional useful photosensitizers include modified forms of oxazines like Nile Blue A. Addition of heavy atomic such as bromine and iodine or in some cases ring substitution of oxygen by sulfur usually enhances in vitro photodynamic activity.

Cincotta et al. have disclosed at Photochem Photobiol 46, 751 (1987). Nile Blue derivatives such as iodinated compounds are useful, as well as certain sulfur derivatives.

Other useful compounds include the phthalocyamines which are an extension of the porphyrin systems.

Still another group of compounds are the naphthalocyanines.

Yet another group of useful compounds include the dihydroporphyrins or chlorins.

Another group of photosensitizers include the ether-substituted pheophorbides and pyropheophorbides.

Activation Components

Activation components are chemical compounds that react to produce light. One well known activation component is aminophthalic hydrazide known as luminol which can be oxidized to produce light. Luminol is also known as 3-amino phthalhydrazide or 3-aminophtholic acid hydrazide or most properly as 5-amino-2,3-dihydrophthalazine-1,4-dione. Luminol and variations thereof are disclosed in detail in the above cited book edited by Burr.

Peroxyoxylate compounds also disclosed by Burr are also useful as activator compounds in the invention.

Liposomes

Although a wide variety of liposomes are capable of use within the techniques of the present invention, the particular liposomes utilized in demonstrating the feasibility of the present invention are termed large unilamellar, or single layer, vesicles (LUV). More specifically, the LUV's employed within the technique of the present invention are made up of a 9:1 weight combination of dipalmitoylphosphatidylcholine (DPPC) and distearoylphosphatidylcholine (DSPC), prepared in a physiological buffer (that is, saline, 10 mM HEPES, pH 7.4). These LUV's were made by reverse phase evaporation using chloroform and isopropyl ether.

Melting of the liposome encapsulated materials is accomplished with direct heat-producing systems, such as Nd-YAG laser, ultrasound, radio-frequency, microwave frequency, all of which are currently in use in humans for hyperthermia treatments and all of which penetrate into tissue from 1-2 cm (Nd-YAG) to whole body (ultrasound).

In pre-clinical studies, it has been possible to demonstrate that the light generated for an activator system consisting of luminol, hemin and hydrogen peroxide can be transferred and/or absorbed by a photosensitizer, such as Photofrin.

An example of how such systems could be used in vivo is as follows: 1) Photofrin photosensitizer is injected into the host one hour to several days prior to activation; 2) heat-sensitive liposomal preparations consisting of dipalmitoylphosphatidylcholine (9 parts) and distearoylphosphatidylcholine (one part) are prepared as described in Radiat. Res. 122: 161, 1990. The components of the activator system, e.g. isobutanal and hemin, are incorporated separately into such liposomes along with any other components required in one or the other liposomal preparation. 3) On the day of treatment, the liposomes are mixed and injected systemically into the host, either as a bolus or continuously. 4) The temperature at the tumor site is increased to 41°–42° C. via appropriate sources noted above and continued until the appropriate activation has occurred (determined from preliminary in vitro experiments). Alternatively, a portion of the activator can be directly attached to the photosensitizer, e.g., the α-hydro-aldehyde part of isobutanal attached to the 2- or 4-position of porphyrins in Photofrin. Thus, only the remaining component(s) of an activator system are necessary and can be packaged into a single liposome and treated as above. Further, in certain cases, a cytotoxic species (e.g. singlet oxygen) can be generated directly at the tumor site by attaching its precursor (as above) to a tumor localizer (e.g. Photofrin or better, certain metallized Photofrins to preclude cutaneous photosensitivity induced by Photofrin itself) and activating at the tumor site as above using the appropriate remaining components of the activator system delivered via heat-sensitive liposomes. An example is the generation of singlet oxygen in high yield from malonaldehyde when oxidized by oxygen in the presence of a peroxidase, for example, hemin or horseradish peroxidase. Attachment of the malonaldehyde structure to Photofrin (or metallo-porphyrins) followed by delivery of the required remaining activator components (a peroxidase and $Mn^{+2}$) via liposome and followed by heat produces singlet oxygen directly.

Numerous other combinations of various photosensitizers and in situ activator systems can be used in the same manner as described above.

EXAMPLES

Following are illustrative examples of the invention which are not intended to limit the invention.

EXAMPLE 1

Heat-sensitive liposome preparations are prepared using dipalmitoylphosphatidyl choline (DPPC), 9 parts, and distearoylphosphatidyl choline (DSPC), 1 part, dissolved in methyl alcohol along with the desired material to be incorporated, evaporating and dispersing in normal saline (1). For light generating systems, separate liposomal preparations are prepared for 4-methoxy-4-(3-phosphatephenyl) spiro [1,2-dioxetane-3, 2'-adamantane] disodium salt and the activating enzyme, alkaline phosphatase. The liposomal preparations are approximately 1 mg/ml in each of the components of the light generating system.

Inbred mice, DBA/2 implanted subcutaneous with mammary tumors (SMT-F) approximately 5 mm in diameter and injected 20–24 hours earlier with 10 mg/kg Photofrin, are treated with the liposomal preparations as follows. Equivalent amounts of the components are diluted in normal saline and slowly administered intravenously via the tail vein using an automatic dispenser delivering approximately 0.1 ml per hour for one hour. Concurrently, the tumor area is warmed to maintain 41° C. at the center of the tumor by means of controlled microwave irradiation monitored via a micro thermocouple. As the liposomal preparations reach the tumor vascular bed and reach 41° C., they are melted causing mixing of the light-generating components and rapid light emission between 460 nm and 680 nm where Photofrin absorbs strongly. The animals are treated similarly on three successive days and followed daily thereafter. In contrast, to control animals treated similarly but not previously injected with Photofrin, tumors in treated mice are found to undergo rapid necrosis and eventual sloughing. This results in complete tumor eradication in at least half the treated animals.

EXAMPLE 2

For enhanced light emission, the experiment is carried out as in Example 1 but 9, 10-dibromoanthracene is incorporated into one of the liposomes also containing a component of the light generating system ($10^{-5}$M) thus allowing use of less of the components (0.01 mg/ml) and reduced normal tissue toxicity. Groups of mice treated with this three component system as in Example 1 are cured of their tumors in 20% of the cases.

EXAMPLE 3

Luminol (aminophthalic hydrazide) is incorporated into heat sensitive liposomes consisting of 9 parts dipalmitoylphosphatidyl choline (DPPC) and 1 part distearoylphosphatidyl choline (DSPC) by dissolving all components in methyl alcohol, evaporating and dispersing in normal saline, as disclosed by Iga, K. et al. in Heat-specific drug release of large unilamellar-vesicle as hyperthermia-mediated targeting delivery. Int. J. Pharm. 57, 241-251, 1989. The final solution is approximately 1 mg/ml in luminol. This mixture is injected into DBA/2 mice bearing subcutaneous mammary tumors (SMT-F) approximately 5 mm in diameter, at a dose of 10 mg/kg. The liposomes are melted at 41° C. in the tumor bed by means of microwave generation and temperature is monitored by means of a micro thermocouple. If the mice have been injected approximately 24 hours earlier with 10.0 mg/kg of Photofrin, tumors turn necrotic within 48 hours and regress in size. No regression occurs if Photofrin has not been injected. If three such treatments are carried out over three successive days in Photofrin injected mice, approximately 50% of animals are free of tumor at 30 days post treatment. No animals are free of tumor at 30 days post treatment if Photofrin is excluded.

I claim:

1. In the process of photodynamic therapy, the improvement comprising:
   1) separately encapsulating at least two activation components for said photodynamic therapy process in a liposome;
   2) injecting a photosensitizer into a human or animal host;
   3) injecting the liposome encapsulated components systemically into the same human or animal host; and
   4) heating the site of the tumor to melt the liposome encapsulated components to permit mixing of the activation components.
2. The process of claim 1 wherein the mixing of the activation components results in energy transfer to the previously injected photosensitizer.
3. The process of claim 1 wherein the mixing of the activation components results in the emission of light and absorption of said light by the previously injected photosensitizer.
4. The process of claim 1 wherein the mixing of the activation components results in direct formation of at least one cytotoxic species that functions against such tumor.
5. The process of claim 1 wherein the heating of the site of the tumor is accomplished by one of the following methods:
   laser, ultra sound, radio-frequency or microwave frequency.
6. The process of claim 1 wherein the photosensitizer is a material capable of being activated by light emission from a luminescent source.
7. The process of claim 1 wherein the photosensitizer is a material capable of accepting energy from the activation components.
8. The process of claim 1 wherein the photosensitizer is a porphyrin.
9. In the process of photodynamic therapy, the improvement comprising:
   1) separately encapsulating at least two activation components for said photodynamic therapy process in a liposome;
   2) injecting a photosensitizer which comprises a porphyrin into a human or animal host;
   3) injecting the liposome encapsulated components systemically into the same human or animal host; and
   4) heating the site of the tumor to melt the liposome encapsulated components to permit mixing of the activation components and generation of light which is absorbed by said photosensitizer.

* * * * *